Figure 3:
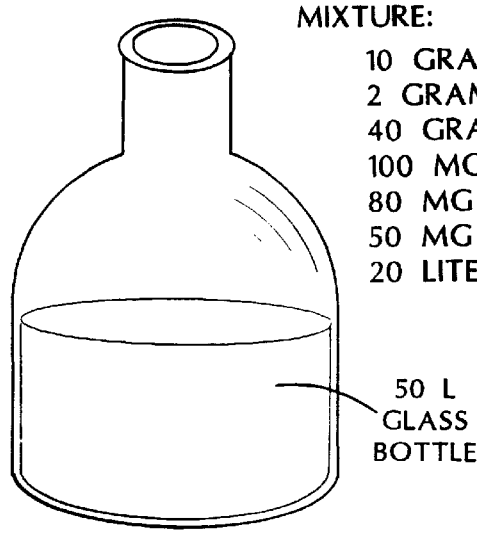

United States Patent [19]
Handelman

[11] Patent Number: 6,075,058
[45] Date of Patent: Jun. 13, 2000

[54] COMPOSITIONS FOR INCREASED BIOAVAILABILITY OF CAROTENOIDS

[75] Inventor: Garry J Handelman, Melrose, Mass.

[73] Assignee: Tufts University, Boston, Mass.

[21] Appl. No.: 09/210,468

[22] Filed: Dec. 12, 1998

[51] Int. Cl.⁷ .................................................. A61K 31/045
[52] U.S. Cl. .............................................................. 514/729
[58] Field of Search ............................................ 514/729

[56] References Cited

FOREIGN PATENT DOCUMENTS

WO 93/04598   3/1993   WIPO .

*Primary Examiner*—Kimberly Jordan
*Attorney, Agent, or Firm*—Fish & Richardson P.C.

[57] ABSTRACT

A mixture of 200 micrograms of the carotenoid lutein and 125 micrograms of the carotenoid zeaxanthin, along with the 10 mg of cholesterol, 100 mg olive oil, 20 mg egg yolk phospholipid, 250 micrograms alpha-tocopherol, and 0.375 ml of 0.15 M aqueous sodium chloride solution. This mixture is prepared by mixing the lipid ingredients into ethanol, evaporating the ethanol, and dispersing the lipids as an emulsion in the sodium chloride solution. The mixture is dispensed into gelatin capsules, and 2 capsules per day provide uptake of the carotenoids into the bloodstream.

14 Claims, 3 Drawing Sheets

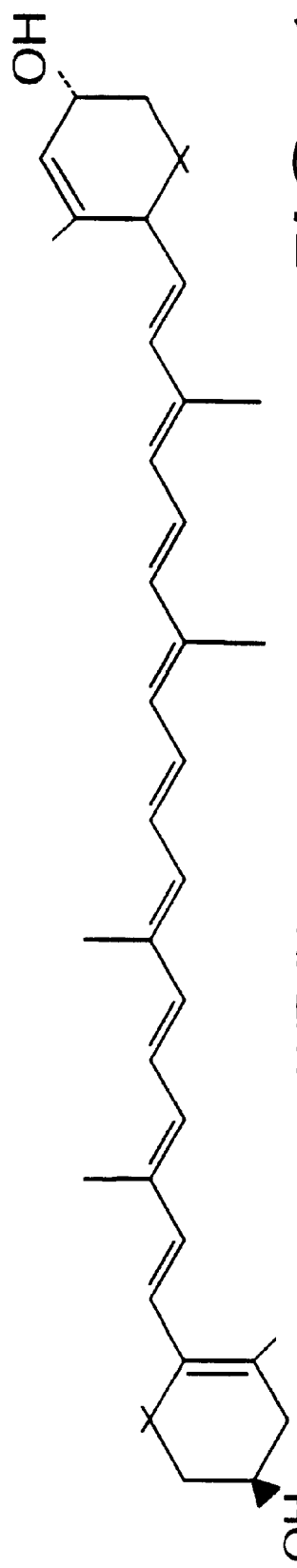
FIG. 1 LUTEIN
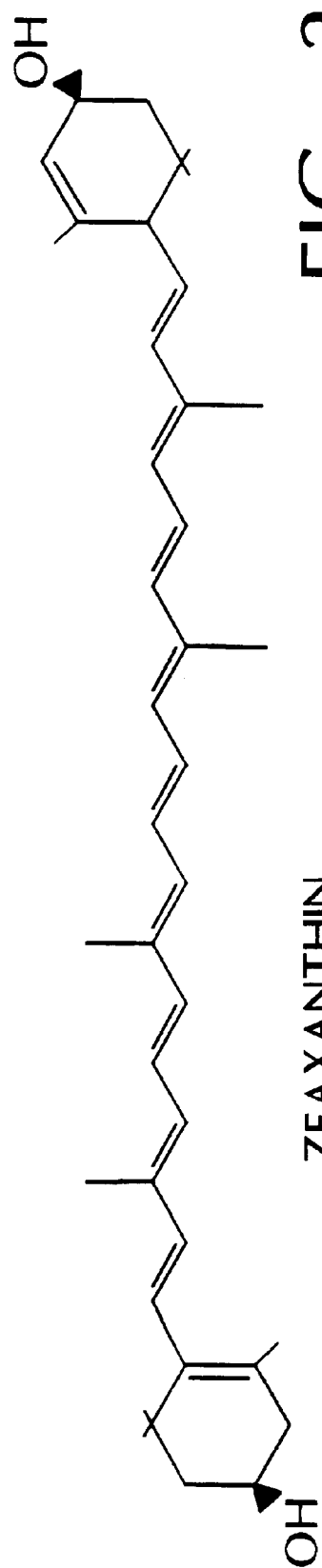
FIG. 2 ZEAXANTHIN

MIXTURE:
- 10 GRAMS EGG PHOSHATIDYL CHLORINE
- 2 GRAMS CHOLESTEROL
- 40 GRAMS OLIVE OIL
- 100 MG ALPHA-TOCOPHEROL
- 80 MG LUTEIN
- 50 MG ZEAXANTHIN
- 20 LITERS ETHANOL

50 L GLASS BOTTLE

500 ML FROM FIG. 3

ROTATION
VACUUM
37°C WATER BATH

LIPIDS ON WALL OF FLASK

LIPIDS DISPENSED
IN 0.15 M
AQUEOUS
SODIUM CHLORIDE

GELATIN CAPSULE
CONTAINING
0.5 ML OF
LIPID EMULSION

COMPOSITIONS FOR INCREASED BIOAVAILABILITY OF CAROTENOIDS

BACKGROUND

1. Field of the Invention

Biochemical research has documented the presence of two carotenoids, lutein and zeaxanthin, at the center of the human retina. This region of the retina is known as the MACULA, and the two carotenoids are known as the MACULAR PIGMENT.

It is desirable to elevate the level of these carotenoids in the bloodstream, since that elevation leads to increased amounts of pigment in the macula. Increased lutein and zeaxanthin in the macula will decrease the risk of macular denegeration, a debilitating and common disease of the elderly.

There is research that indicates that lutein and zeaxanthin have are protective against heart disease and cancer in humans.

There are a number of food sources that contain lutein and zeaxanthin, but for many of these food sources, absorption into the bloodstream is not efficient. For example, corn contains ample amounts of zeaxanthin, but it is difficult to elevate plasma zeaxanthin by consuming corn.

2. Prior Art

Other investigators have attempted to maximize the absorption of these carotenoids by use of a special matrix. Snodderly and coworkers (see reference below) prepared zeaxanthin in a special carbohydrate matrix, and attempted to raise the zeaxanthin levels of monkeys. To achieve a doubling of plasma levels, they had to adminster a daily dose of 1 mg/kg body weight, a dose 100×larger than is needed for humans if the zeaxanthin is dispersed in egg yolk.

Therefore, prior art indicates that the correct matrix might be effective at raising plasma zeaxanthin levels, but no prior art addresses the specific matrix of triglyceride, phospholipid and cholesterol which is the basis of this invention. This invention is fully novel because it addresses the specific matrix of triglyceride, phospholipid and cholesterol as a means of gaining efficient absorption of dietary lutein and zeaxanthin into the bloodstream.

Reference: Snodderly D M, Shen B, Land R I, Krinsky N I. Dietary manipulation of plasma carotenoid concentrations of squirrel monkeys (*Saimiri sciureus*). J Nutr 1997; 127:122–129.

OBJECTS AND ADVANTAGES a) This invention will allow efficient increase in plasma and retinal levels of the carotenoids lutein and xeaxanthin, with the use of small doses.

b) Since these carotenoids are costly, this will achieve bloostream levels similar to one chicken egg per day with minimal use of the material.

c) Large doses of carotenoids may be toxic. Since this invention allows the use of the small dosages typical of the amount obtained from one egg/day, toxicity from high doses of carotenoids is avoided.

d) The amount of dietary cholesterol found in one egg per day can be harmful. This invention achieves the same effect on plasma lutein and zeaxanthin as is obtained with 1 egg/day, but the invention adds 20 mg of cholesterol to daily intake. By contrast, one egg adds 200 mg of cholesterol to daily dietary intake.

e) The increased lutein and zeaxanthin in the plasma will lead to elevated levels of these carotenoids in the macula, and other tissues, providing protection against macular degeneration, cancer and heart disease. The low doses needed, and small amount of cholesterol in the product, are advantageous in terms of cost and safety.

BRIEF DESCRIPTION OF THE DRAWING FIGURES

FIG. 1 Lutein.

FIG. 2 Zeaxanthin.

FIG. 3 Mixing lipid ingredients with ethanol in 50 liter flask.

Figure 4:
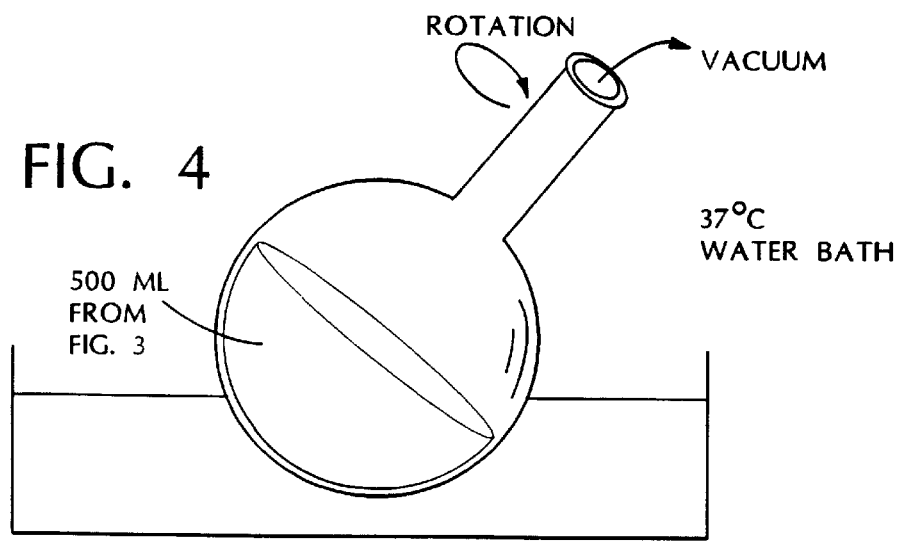

FIG. 4 Evaporating portions of the mixture in ethanol under vacuum at 37° C.

Figure 5:
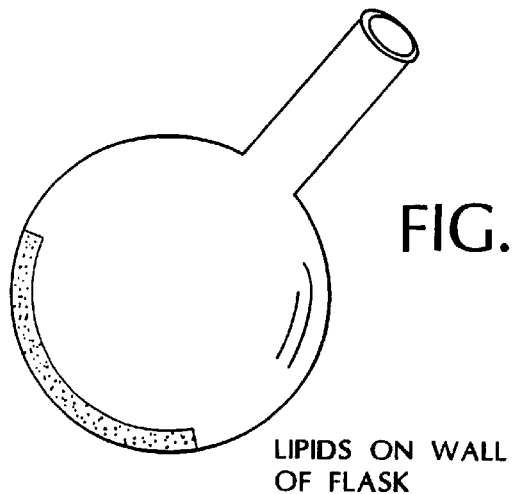

FIG. 5 Lipid residue obtained after evaporation.

Figure 6:
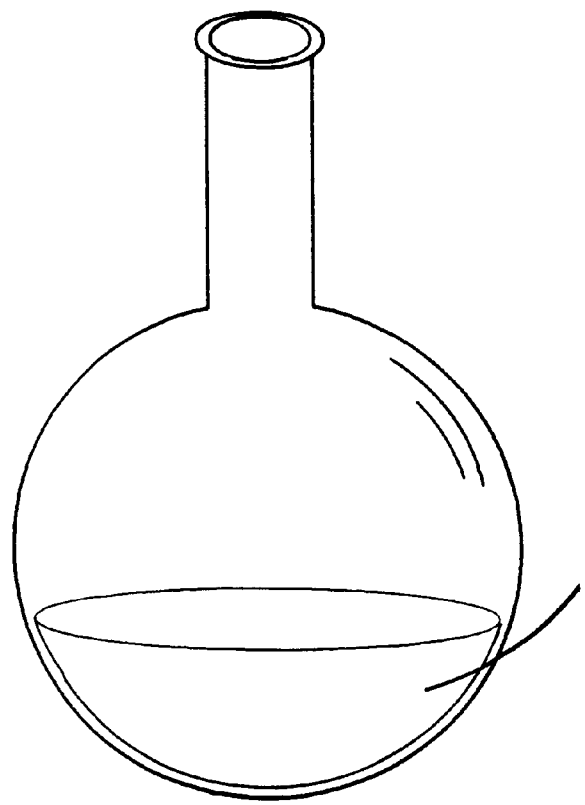

FIG. 6 Preparation of lipid emulsion in aqueous sodium chloride solution.

Figure 7:
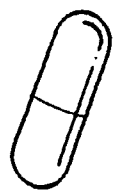

FIG. 7 Capsules containing lipid emulsion for use as dietary supplement.

SUMMARY

The carotenoids lutein and zeaxanthin are mixed with olive oil, egg yolk phospholipid, and cholesterol, and alpha-tocopherol, and dispersed as an emulsion in saline solution. This mixture is then administered as dietary supplement, and allows efficient uptake of the carotenoids into the bloodstream.

MAIN EMBODIMENT—TECHNICAL DESCRIPTION

A. MATERIALS USED FOR THE INVENTION

1. Egg phospatidylcholine, food grade 10 grams
2. Cholesterol, USP 2 grams
3. Olive oil, food grade 40 grams
4. Alpha-tocopherol, USP 100 mg
5. Lutein, food-grade 80 mg
6. Zeaxanthin, food-grade 50 mg
7. Ethanol, USP 20 liters
8. Sodium chloride, aqueous 0.15 M, USP 150 ml

B. PREPARATION OF THE INVENTION

1. The lipid materials (all materials except the sodium chloride solution) are mixed at room temperature in a 50 liter glass container, to dissolve all the components in the ethanol.

2. Portions of the mixture (500 ml) are transferred to a round bottom flask. The ethanol is evaporated with a vacuum, while heating at 37 C. in a water bath.

3. After the ethanol is removed, additional portions are transferred to the flask, and the ethanol evaporated. This is continued until all the materials are transferred to the round-bottom flask.

4. When all the material is deposited as a mixture on the wall of the flask, 150 ml of sodium chloride solution is added to the flask.

5. The flask is agitated, while heating to 37 C., to create an emulsion that contains all the lipid ingredients mixed together. The final volume of the emulsion is 200 ml.

6. This emulsion is dispensed into 0.50 ml capsules. Two capsules contain 1 ml of the emulsion.

7. Two capsules are administered as a daily dietary supplement.

C. DESCRIPTION OF CAPSULE CONTENTS

Two capsules are a customary dose. This dose contains:

1. Lutein, 400 micrograms
2. Zeaxanthin, 250 micrograms
3. Alpha-tocopherol, 500 micrograms
4. Cholesterol, 20 mg
5. Olive oil, 400 mg
6. Lecithin, 100 mg
7. Sodium chloride solution, 0.75 ml.

Thus, two capsules provide as much lutein and zeaxanthin as a large egg from corn-fed chickens. However, the cholesterol content has been reduced from 200 mg to 20 mg.

I claim:

1. A composition consisting essentially of a carotenoid, cholesterol, a triglyceride, and a phospholipid, wherein at least 15% of said composition by weight is a phospholipid.

2. The composition of claim 1, wherein said composition consists essentially of a carotenoid, 20 milligrams of cholesterol, 400 milligrams of a triglyceride, and 100 milligrams of a phospholipid.

3. The composition of claim 1, wherein said triglyceride is olive oil and said phospholipid is lecithin.

4. The composition of claim 1, wherein the composition consists essentially of 400 micrograms of lutein, 250 micrograms of zeaxanthin, 20 milligrams of cholesterol, 400 milligrams of olive oil, and 100 milligrams of lecithin.

5. The composition of claim 1, wherein said triglyceride comprises olive oil and alpha-tocopherol.

6. The composition of claim 1, wherein said composition consists essentially of 400 micrograms of lutein, 250 micrograms of zeaxanthin, 20 milligrams of cholesterol, 400 milligrams of olive oil, 500 micrograms of alpha-tocopherol, and 100 milligrams of lecithin.

7. A composition consisting essentially of a carotenoid, cholesterol, a triglyceride, and a phospholipid, wherein at least 19% by weight of said composition is a phospholipid.

8. The composition of claim 7, wherein said composition consists essentially of a carotenoid, 10 milligrams of cholesterol, 100 milligrams of a triglyceride, and 20 milligrams of a phospholipid.

9. The composition of claim 7, wherein said triglyceride is olive oil and said phospholipid is lecithin.

10. The composition of claim 7, wherein said composition consists essentially of 200 micrograms of lutein, 125 micrograms of zeaxanthin, 10 milligrams of cholesterol, 100 milligrams of olive oil, and 20 milligrams of lecithin.

11. The composition of claim 7, wherein said triglyceride comprises olive oil and alpha-tocopherol.

12. The composition of claim 7, wherein said composition consists essentially of 200 micrograms of lutein, 125 micrograms of zeaxanthin, 10 milligrams of cholesterol, 100 milligrams of olive oil, 250 micrograms of alpha-tocopherol, and 20 milligrams of lecithin.

13. A method of elevating the level of a carotenoid in a tissue of an animal comprising administering to said animal the composition of claim 1.

14. A method of elevating the level of a carotenoid in a tissue of an animal comprising administering to said animal the composition of claim 7.

* * * * *

UNITED STATES PATENT AND TRADEMARK OFFICE
CERTIFICATE OF CORRECTION

PATENT NO. : 6,075,058
DATED : June 13, 2000
INVENTOR(S) : Garry J. Handelman

It is certified that error appears in the above-identified patent and that said Letters Patent is hereby corrected as shown below:

Column 1,
Line 5, after Background, insert as a new paragraph,

-- This invention was made with government support under grant no. 58-1950-9-001 awarded by the United States Department of Agriculture. The government has certain rights in the invention --.

Signed and Sealed this

Fourth Day of December, 2001

*Attest:*

NICHOLAS P. GODICI
*Attesting Officer*   Acting Director of the United States Patent and Trademark Office